(12) United States Patent
Gliner et al.

(10) Patent No.: US 10,803,645 B2
(45) Date of Patent: *Oct. 13, 2020

(54) VISUALIZATION OF ANATOMICAL CAVITIES

(71) Applicant: Biosense Webster (Israel) Ltd., Yokneam (IL)

(72) Inventors: Vadim Gliner, Haifa (IL); Andres Claudio Altmann, Haifa (IL); Ram Bernard Mayer, Raanana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/661,116

(22) Filed: Oct. 23, 2019

(65) Prior Publication Data

US 2020/0118319 A1 Apr. 16, 2020

Related U.S. Application Data

(63) Continuation of application No. 15/364,144, filed on Nov. 29, 2016, now Pat. No. 10,510,171.

(51) Int. Cl.
| | |
|---|---|
| *A61B 34/10* | (2016.01) |
| *A61B 34/20* | (2016.01) |
| *G06T 19/20* | (2011.01) |
| *G06T 11/40* | (2006.01) |
| *A61B 17/24* | (2006.01) |
| *G06T 11/60* | (2006.01) |
| *A61B 6/02* | (2006.01) |

(Continued)

(52) U.S. Cl.
CPC ............... *G06T 11/60* (2013.01); *A61B 6/02* (2013.01); *A61B 6/466* (2013.01); *A61B 8/469* (2013.01); *A61B 34/10* (2016.02); *A61B 34/20* (2016.02); *A61B 34/25* (2016.02); *G01N 23/046* (2013.01); *G06T 11/001* (2013.01); *G06T 11/003* (2013.01); *G06T 11/40* (2013.01); *G06T 19/20* (2013.01); *A61B 17/24* (2013.01); *A61B 2034/101* (2016.02); *A61B 2034/105* (2016.02); *A61B 2034/107* (2016.02); *A61B 2034/2051* (2016.02); *A61B 2034/252* (2016.02); *A61B 2090/374* (2016.02); *A61B 2090/3762* (2016.02); *G01N 2223/419* (2013.01); *G06F 2111/10* (2020.01); *G06T 2210/41* (2013.01); *G06T 2219/2012* (2013.01); *G06T 2219/2021* (2013.01)

(58) Field of Classification Search
CPC .............................. G06T 11/60; G06T 11/001
See application file for complete search history.

(56) References Cited

U.S. PATENT DOCUMENTS

2009/0148012 A1* 6/2009 Altmann .................. A61B 5/06
382/128
2009/0252395 A1* 10/2009 Chan ...................... A61B 6/466
382/131
(Continued)

*Primary Examiner* — Jitesh Patel
(74) *Attorney, Agent, or Firm* — Frost Brown Todd LLC

(57) ABSTRACT

Described embodiments include a system that includes a display and a processor. The processor is configured to modify an image slice by filling a portion, of the image slice, that corresponds to an anatomical cavity with a representation of a wall of the anatomical cavity, and to display the modified image slice on the display. Other embodiments are also described.

20 Claims, 2 Drawing Sheets

(51) Int. Cl.
  *A61B 6/00*     (2006.01)
  *G01N 23/046*   (2018.01)
  *G06T 11/00*    (2006.01)
  *A61B 34/00*    (2016.01)
  *A61B 8/00*     (2006.01)
  *A61B 90/00*        (2016.01)
  *G06F 111/10*       (2020.01)

(56)     References Cited

U.S. PATENT DOCUMENTS

2012/0203530 A1* 8/2012 Sharma .................. G16H 50/50
                                                      703/9
2015/0038860 A1* 2/2015 Fonte ....................... A61B 6/50
                                                      600/505
2016/0120609 A1* 5/2016 Jacobsen ................ A61B 5/062
                                                      600/424
2017/0011197 A1* 1/2017 van Dam ................ G06F 19/00

* cited by examiner

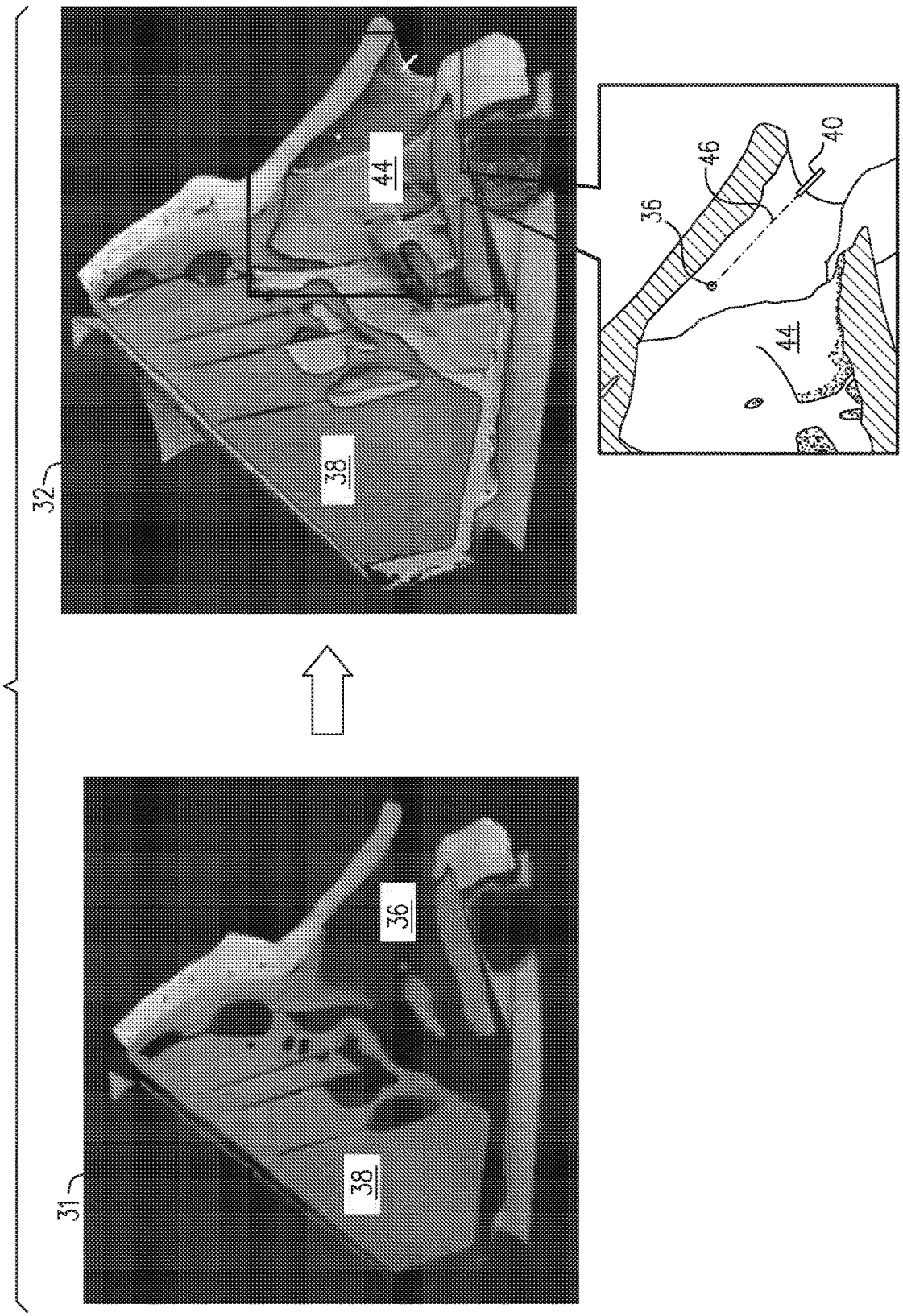

VISUALIZATION OF ANATOMICAL CAVITIES

CROSS REFERENCE TO RELATED APPLICATIONS

The present application is a continuation of U.S. patent application Ser. No. 15/364,144, entitled "Visualization of Anatomical Cavities," filed Nov. 29, 2016, issued on Dec. 17, 2019 as U.S. Pat. No. 10,510,171, which itself is related to an application entitled "Visualization of distances to walls of anatomical cavities," U.S. patent application Ser. No. 15/364,156, filed Nov. 29, 2016, published as U.S. Pub. No. 2018/0146884 on May 31, 2018, the disclosure of each of which is incorporated herein by reference.

FIELD OF THE INVENTION

The present invention relates to the field of medical images.

BACKGROUND

A computerized tomography (CT) scan acquires the radiodensity, also termed radiopacity, of the scanned portion of anatomy. Radiodensity is measured in Hounsfield units (HU), with air having HU=−1000, water having HU=0, and cortical bone having HU=+3000. In a CT image, the acquired radiodensity values are mapped to different gray-scale values. Typically, in a CT image, air is presented in black, cortical bone in white, and other materials in varying shades of gray.

Traditionally, interventional radiologists have been trained to navigate the head of a subject using two-dimensional (2D) images of the head. For example, during a sinus procedure, the interventional radiologist may refer to three computerized tomography (CT) slices of the subject's head: an axial slice, a coronal slice, and a sagittal slice.

U.S. Pat. No. 8,532,738, whose disclosure is incorporated herein by reference, describes a method, including constructing a simulated surface of a body cavity, and pressing a distal end of a probe against a wall of the body cavity. While pressing the distal end against the wall, position measurements are accepted from the probe indicating a position of the probe within the body cavity, and force measurements are accepted from the probe indicating a force between the distal end and the wall. A distortion in the simulated surface is created at the position indicated by the position measurements, so as to form a distorted surface, upon detecting that the force measurements exceed a predefined amount. The distorted surface is then displayed.

U.S. Pat. No. 7,924,279, whose disclosure is incorporated herein by reference, describes a system for visualizing a 3D volume, in particular for medical applications, that includes an input for receiving a three-dimensional set of data representing voxel values of the 3D volume. The data set is stored in a storage. A processor projects the volume onto an imaginary 2D projection screen from a predetermined viewpoint. For each pixel of the 2D projection image a ray is cast through the pixel and through the volume. A protocol is used that, while traversing along ray positions within the volume, determines a rendering algorithm and/or rendering parameters in dependence on the ray position. For each ray position the determined rendering algorithm/parameters are used to calculate a contribution to a pixel value of the pixel based on at least one voxel value within a predetermined range of the ray position. An output is used for providing pixel values of a 2D image for rendering on a display.

SUMMARY OF THE INVENTION

There is provided, in accordance with some embodiments of the present invention, a system that includes a display and a processor. The processor is configured to modify an image slice by filling a portion, of the image slice, that corresponds to an anatomical cavity with a representation of a wall of the anatomical cavity, and to display the modified image slice on the display.

In some embodiments, the processor is further configured to identify the portion of the image slice that corresponds to the anatomical cavity.

In some embodiments, the processor is configured to modify the portion of the image slice that corresponds to the anatomical cavity without modifying other portions of the image slice.

In some embodiments, the processor is further configured to compute the representation by rendering the wall of the cavity.

In some embodiments, the processor is configured to render the wall of the cavity in color.

In some embodiments, the wall of the cavity is located behind a location at which the image slice was acquired.

In some embodiments, the image slice is a computed tomography (CT) image slice.

In some embodiments, the processor is further configured to overlay an icon that represents an intrabody tool on a portion of the modified image slice that corresponds to a location of the intrabody tool within the anatomical cavity.

In some embodiments, the processor is further configured to overlay a marker on a portion of the representation of the wall that corresponds to a location at which the intrabody tool would meet the wall, were the intrabody tool to continue moving toward the wall in a direction in which the intrabody tool is pointing.

In some embodiments, the processor is further configured to identify the location at which the intrabody tool would meet the wall, by projecting a virtual ray from a distal tip of the intrabody tool.

There is further provided, in accordance with some embodiments of the present invention, a method that includes, using a processor, modifying an image slice by filling a portion, of the image slice, that corresponds to an anatomical cavity with a representation of a wall of the anatomical cavity, and displaying the modified image slice.

The present invention will be more fully understood from the following detailed description of embodiments thereof, taken together with the drawings, in which:

BRIEF DESCRIPTION OF THE DRAWINGS

FIG. 2 shows an original CT image slice and a modified CT image slice, in accordance with some embodiments of the present invention.

DETAILED DESCRIPTION OF EMBODIMENTS

Overview

Figure 1:
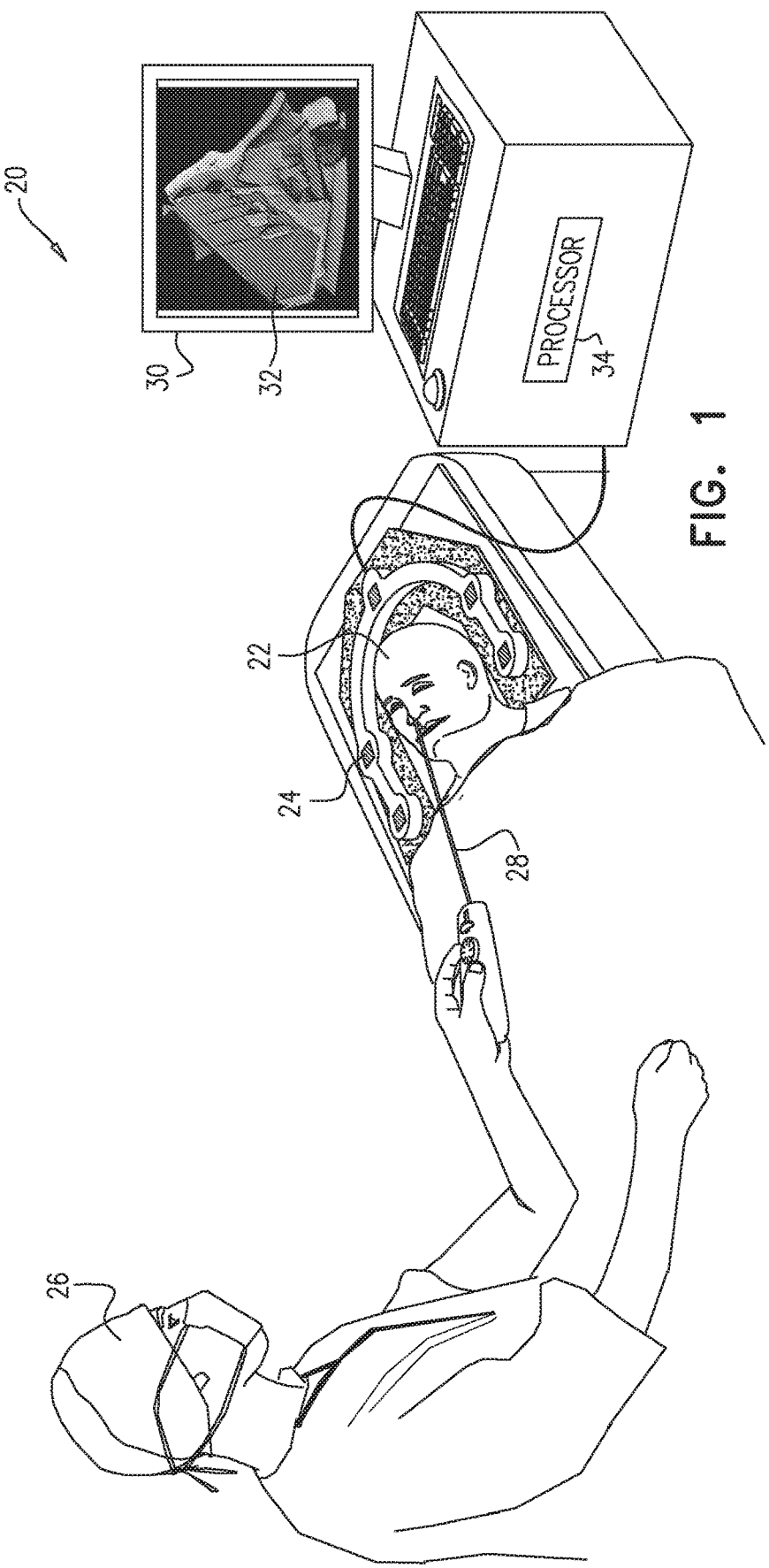
FIG. 1 is a schematic illustration of a system for guiding a medical procedure, in accordance with some embodiments of the present invention.

As noted above, interventional radiologists typically use 2D images (or "slices") for navigation. A challenge in using 2D images, however, is the lack of depth information contained in such images. For example, when using 2D images to navigate a catheter within an anatomical cavity, it may be difficult to ascertain the distance between the catheter and the wall of the cavity.

Embodiments of the present invention address this challenge, by providing an enhanced presentation of anatomical cavities in 2D images. In this enhanced presentation, the cavity is given a three-dimensional (3D) appearance, via the incorporation of morphological information from beneath the displayed 2D slice. For example, a processor may "illuminate" the cavity with a virtual light source, such that the walls of the cavity, beneath the displayed 2D slice, are "visible" to a virtual camera positioned near the virtual light source. The cavity walls may then be rendered, in color, with varying shades of brightness, corresponding to the view of the virtual camera.

Some embodiments enhance the image further, by overlaying, on the image, an icon that represents the catheter, along with a marker that indicates the distance of the catheter from the cavity wall. To produce the marker, a processor may project a virtual ray from the tip of the catheter, and show the marker, in the image, at the point at which the virtual ray hits the cavity wall.

System Description

Reference is initially made to FIG. 1, which is a schematic illustration of a system 20 for guiding a medical procedure, in accordance with some embodiments of the present invention.

FIG. 1 depicts a physician 26 performing a procedure on a subject 22. During this procedure, physician 26 inserts an intrabody tool 28, such as a catheter, into a nasal cavity and/or a sinus of subject 22, and then uses tool 28 to probe, and/or operate on, the nasal cavity and/or sinus. Typically, the location and orientation of the tool is tracked, using, for example, a magnetic tracking system. For example, system 20 may comprise one or more magnetic-field generators 24, which, during the procedure, generate respective magnetic fields. These fields induce respective voltages in one or more magnetic sensors coupled to tool 28. Based on these induced voltages, a processor 34 ascertains the location and orientation of the tool with respect to the coordinate system of the tracking system.

Typically, prior to the procedure, a volume of the subject's head is acquired, using, for example, a CT scanner. Subsequently, during the procedure, processor 34 displays, on a display 30, at least one image slice 32, taken from the volume and enhanced as described below. The physician may then refer to slice 32, in deciding how to best navigate the subject's nasal cavity and/or sinus.

It is noted that the term "image slice," as used in the present application (including the claims), refers to any two-dimensional image acquired by imaging a particular cross-section of a three-dimensional object, or by taking a particular cross-section of a three-dimensional image of the object. (An image slice may be alternatively referred to herein simply as an "image" or a "slice.") For example, prior to the procedure, a volume of the subject's head may be acquired, by acquiring a stack of sagittal image slices at successive depths. Subsequently, processor 34 may derive an "image slice" from this volume, by taking any one of the original sagittal image slices from the volume, or by taking a cross-section of the volume such as to derive a new slice having another suitable orientation. (Typically, the derivation of new slices is performed prior to the procedure.)

Typically, prior to the procedure, processor 34 registers the magnetic tracking system with the CT scanner, e.g., as described in U.S. patent application Ser. No. 15/290,968, issued as U.S. Pat. No. 10,152,786 on Dec. 11, 2018, whose disclosure is incorporated herein by reference. The output of this registration procedure is a transformation, which the processor subsequently uses to compute the location of the distal end of the intrabody tool with respect to image slice 32.

In general, processor 34 may be embodied as a single processor, or as a cooperatively networked or clustered set of processors. Processor 34 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Reference is now made to FIG. 2, which shows an original CT image slice 31 and a modified CT image slice 32, in accordance with some embodiments of the present invention.

As described above, a CT image typically presents air in black, cortical bone in white, and other materials in varying shades of gray. For example, image slice 31 includes a black portion, referred to herein as a void 36, corresponding to an anatomical cavity; in particular, void 36 corresponds to a nasal cavity of the subject. (In other words, image slice 31 "slices through" the nasal cavity, such that the interior of the nasal cavity appears in the image slice as void 36.) Image slice 31 further includes a white or gray region 38, corresponding to bone and/or other tissue surrounding the nasal cavity.

In embodiments of the present invention, processor 34 modifies image slice 31, such as to generate modified image slice 32. To modify image slice 31, the processor first identifies portions of image slice 31 that correspond to anatomical cavities, i.e., that were formed by the intersection of the scan plane of the scanner with the anatomical cavities. (As described above, in CT images, these portions appear as voids, such as void 36.) The processor then fills each of the identified portions with a representation of a wall of the corresponding anatomical cavity, thus giving each anatomical cavity a three-dimensional appearance. (Stated differently, the processor overlays, on each identified portion of the image, a three-dimensional (3D) view of the corresponding anatomical cavity.) For example, in modified image slice 32, void 36 is replaced with a three-dimensional representation 44 of the wall of the nasal cavity that is behind the location at which the image slice was acquired (i.e., the wall is behind the scan plane, relative to the perspective of one who views the image) The processor then displays modified image slice 32, as described above with reference to FIG. 1.

More generally, the processor may perform the modification described herein for each image slice that shows part of an anatomical cavity. Typically, prior to the procedure, the processor iterates over all of the relevant image slices (both original and derived), and modifies each cavity-containing image slice as described herein. Subsequently, during the procedure, the processor continually monitors the location of the tool, and, if the location of the tool has changed, the processor may retrieve and display one or more modified image slices that pass through the new location of the tool. (It is noted that the processor may alternatively modify an image slice, as described herein, in real-time, immediately prior to displaying the image slice.)

Typically, the processor computes representation 44, by rendering the wall of the cavity. First, the processor ascertains the form of the wall from the three-dimensional image from which image slice 31 was derived. The processor then uses any suitable rendering technique to render the wall. For example, the processor may illuminate the wall with a virtual light source, and render the wall in accordance with the view of a virtual camera positioned near the virtual light source. The processor then replaces the void in image slice 31 with the rendering. Typically, the wall is rendered in color, to help the physician differentiate between the anatomical cavity and the surrounding tissue.

Typically, the processor does not modify other portions of image slice 31, such as region 38 of the image slice. For example, the processor may not modify any portion of the image slice, other than the portion corresponding to the anatomical cavity. Modified image slice 32 is thus, typically, a "hybrid" image, in that region 38 is shown as a two-dimensional surface, in grayscale, while the wall of the anatomical cavity is rendered as a three-dimensional surface, typically in color.

Reference is now specifically made to the schematic illustration at the bottom of FIG. 2, which reproduces a portion of modified image slice 32.

Typically, the processor further overlays, on modified image slice 32, an icon 40 that represents intrabody tool 28 (in particular, the distal end thereof) on a portion of modified image slice 32 that corresponds to the location of the intrabody tool within the anatomical cavity. Typically, the processor also overlays a marker 42 on a portion of representation 44 that corresponds to a location at which the intrabody tool would meet the wall, were the intrabody tool to continue moving toward the wall in the direction in which the intrabody tool is pointing. For example, the processor may project a virtual ray 46 from the distal tip of the intrabody tool, identify the location at which virtual ray 46 meets the wall of the anatomical cavity, and then overlay marker 42 on the portion of representation 44 that corresponds to this location. (Although, for the sake of illustration, virtual ray 46 is shown in the schematic portion of FIG. 2, it is noted that virtual ray 46 is typically not shown in modified image slice 32.) Icon 40, and marker 42, generally facilitate navigation of the tool within the anatomical cavity, in that, for example, the distance between icon 40 and marker 42 indicates the distance of the tool from the wall of the cavity.

In some embodiments, a fully three-dimensional image (i.e., an image that is fully rendered in three dimensions) is displayed, instead of modified image slice 32 (which, as described above, is only partly rendered in three dimensions), and icon 40 and/or marker 42 are overlaid on the representation of the anatomical wall in this image.

Although the description herein mainly relates to CT images, it is noted that embodiments of the present invention may also be applied to images acquired using other modalities, such as magnetic resonance imaging (MRI). (In MRI images, anatomical cavities do not necessarily appear as voids, but are nonetheless generally identifiable, such that they may be identified and modified as described herein.)

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system comprising:
   (a) a display;
   (b) a memory configured to store an image and a three-dimensional model of a patient anatomy, wherein the image is a two-dimensional image, and wherein a perspective of the patient anatomy shown by the image is present within the three-dimensional model; and
   (c) a processor, configured to:
      (i) identify a portion of the image that corresponds to an anatomical cavity,
      (ii) identify a wall of the three-dimensional model that corresponds to the anatomical cavity, from the same perspective as that of the image,
      (iii) create a hybrid image by overlaying the wall on the anatomical cavity of the image,
      (iv) display the hybrid image on the display, and
      (v) receive output from one or more positions sensors of an intrabody tool and overlay an icon that represents the intrabody tool on a portion of the hybrid image that corresponds to a location of the intrabody tool within the anatomical cavity based on the output.

2. The system according to claim 1, wherein the hybrid image is identical to the image, except for the area that corresponds to the anatomical cavity.

3. The system according to claim 1, wherein the processor is further configured to render the wall in three dimensions and render the remainder of the hybrid image in two dimensions.

4. The system according to claim 3, wherein the processor is further configured to render the wall in color, with varying shades of brightness that provide an indication of depth.

5. The system of claim 1, wherein the processor is further configured to:
   (i) direct a virtual light source at the hybrid image,
   (ii) direct a virtual camera at the hybrid image, and
   (iii) render the wall of the hybrid image in accordance with the view of the virtual camera and the effect of the virtual light source.

6. The system of claim 5, wherein the processor is further configured to, when rendering the wall of the hybrid image in accordance with the view of the virtual camera and the effect of the virtual light source, render the portion in varying shades of brightness.

7. The system of claim 6, wherein the processor is further configured to render the hybrid image in color and render other portions of the hybrid image in grayscale.

8. The system of claim 1, wherein the image is a computed tomography (CT) image slice from a set of CT image slices associated with the patient anatomy, and wherein the processor is further configured to, prior to a surgical procedure associated with the patient anatomy, produce a set of hybrid images based on the set of CT image slices and the three dimensional mode.

9. The system according to claim 1, wherein the processor is further configured to overlay the icon on a portion of the hybrid image that corresponds to a location of a distal tip of the intrabody tool within the anatomical cavity.

10. The system according to claim 9, wherein the processor is further configured to overlay a marker on the hybrid image on a portion of the wall that corresponds to a location at which the intrabody tool would meet the wall, were the intrabody tool to continue moving toward the wall in a direction in which the intrabody tool is pointing.

11. The system according to claim 10, wherein the processor is further configured to:
(i) identify the location at which the intrabody tool would meet the wall by projecting a virtual ray from a distal tip of the intrabody tool, and
(ii) overlay a graphical representation of the virtual ray on the hybrid image that begins at the icon and terminates at the marker.

12. The system of claim 10, wherein the processor is further configured to display a subsequent hybrid image in response to a change in the location of the intrabody tool, wherein the subsequent hybrid image comprises an updated icon and an updated marker based on the change in the location of the intrabody tool.

13. The system of claim 12, wherein the processor is further configured to create the hybrid image and the subsequent hybrid image in real-time, during a procedure, in response to changes in the location of the intrabody tool.

14. A method for performing a procedure on a patient anatomy using an intrabody tool having one or more position sensors, the method comprising:
(a) storing an image and a three-dimensional model of a patient anatomy, wherein the image is a two-dimensional image, and wherein a perspective of the patient anatomy shown by the image is present within the three-dimensional model;
(b) using a processor, identifying a portion of the image that corresponds to an anatomical cavity;
(c) identifying a wall of the three-dimensional model that corresponds to the anatomical cavity, from the same perspective as that of the image;
(d) creating a hybrid image slice by overlaying the wall on the anatomical cavity of the image;
(e) displaying the hybrid image slice; and
(f) receiving output from one or more positions sensors of an intrabody tool and overlaying an icon that represents the intrabody tool on a portion of the hybrid image that corresponds to a location of the intrabody tool within the anatomical cavity based on the output.

15. The method according to claim 14, further comprising rendering the wall of the hybrid image in three dimensions and rendering the remainder of the hybrid image in two dimensions.

16. The method according to claim 15, wherein rendering the wall in three dimensions comprises rendering the wall in color, with varying shades of brightness that provide an indication of depth.

17. The method according to claim 14, further comprising overlaying the icon on a portion of the hybrid image that corresponds to a location of a distal tip of the intrabody tool within the anatomical cavity.

18. The method according to claim 17, further comprising overlaying a marker on a portion of the wall that corresponds to a location at which the intrabody tool would meet the wall, were the intrabody tool to continue moving toward the wall in a direction in which the intrabody tool is pointing.

19. The method according to claim 18, further comprising:
(a) identifying the location at which the intrabody tool would meet the wall by projecting a virtual ray from a distal tip of the intrabody tool; and
(b) overlaying a graphical representation of the virtual ray on the hybrid image that begins at the icon and terminates at the marker.

20. An intrabody navigation system comprising a processor, wherein the processor is configured to:
(i) receive an image and a three-dimensional model of a patient anatomy, wherein the image is a two-dimensional image, and wherein a perspective of the patient anatomy shown by the image is present within the three-dimensional model,
(ii) identify a portion of the image that corresponds to an anatomical cavity,
(iii) identify a wall of the three-dimensional model that corresponds to the anatomical cavity, from the same perspective as that of the image,
(iv) create a hybrid image by overlaying the wall on the anatomical cavity of the image,
(v) receive a set of position data indicating a position of an intrabody tool relative to the patient anatomy,
(vi) overlay an indicator on the hybrid image corresponding to the position of the intrabody tool based on the set of position data, and
(vii) provide the hybrid image to a display.

* * * * *